(12) United States Patent
McFadden et al.

(10) Patent No.: US 9,248,091 B2
(45) Date of Patent: Feb. 2, 2016

(54) NAIL POLISH COMPOSITION AND METHOD OF MAKING A NAIL POLISH

(71) Applicant: MYCONE DENTAL SUPPLY CO., INC., Cherry Hill, NJ (US)

(72) Inventors: Dawn McFadden, Newtown, PA (US); Larry Steffier, Cherry Hill, PA (US)

(73) Assignee: Mycone Dental Supply Co., Inc., Cherry Hill, NJ (US)

( * ) Notice: Subject to any disclaimer, the term of this patent is extended or adjusted under 35 U.S.C. 154(b) by 0 days.

(21) Appl. No.: 14/279,878

(22) Filed: May 16, 2014

(65) Prior Publication Data

US 2014/0341824 A1    Nov. 20, 2014

Related U.S. Application Data

(60) Provisional application No. 61/824,665, filed on May 17, 2013.

(51) Int. Cl.

| | |
|---|---|
| *A61K 9/00* | (2006.01) |
| *A61K 8/73* | (2006.01) |
| *A61Q 3/02* | (2006.01) |
| *A61K 8/26* | (2006.01) |
| *A61K 8/87* | (2006.01) |
| *A61K 8/04* | (2006.01) |

(52) U.S. Cl.
CPC ............. *A61K 8/731* (2013.01); *A61K 8/044* (2013.01); *A61K 8/26* (2013.01); *A61K 8/87* (2013.01); *A61Q 3/02* (2013.01)

(58) Field of Classification Search
CPC ....................................................... A61K 8/731
See application file for complete search history.

(56) References Cited

U.S. PATENT DOCUMENTS

| | | | |
|---|---|---|---|
| 3,422,185 A | 1/1969 | Kuritzkes | |
| 3,864,294 A | 2/1975 | Busch, Jr. | |
| 3,917,556 A * | 11/1975 | Baurecht et al. | 524/376 |
| 4,222,908 A | 9/1980 | Ikeda et al. | |
| 4,229,227 A | 10/1980 | Ikeda et al. | |
| 4,740,370 A | 4/1988 | Faryniarz et al. | |
| 4,822,423 A | 4/1989 | Soyama et al. | |
| 5,071,639 A | 12/1991 | Soyama et al. | |
| 6,814,797 B2 | 11/2004 | Kaneko et al. | |
| 2001/0002253 A1 | 5/2001 | Farer et al. | |
| 2004/0122152 A1 | 6/2004 | SenGupta et al. | |
| 2007/0071703 A1 | 3/2007 | Lin | |
| 2009/0047228 A1 | 2/2009 | Guerchet et al. | |
| 2009/0104134 A1 | 4/2009 | SenGupta et al. | |
| 2010/0196294 A1 * | 8/2010 | Amato et al. | 424/61 |
| 2011/0256079 A1 | 10/2011 | Kozachek | |
| 2011/0274634 A1 | 11/2011 | Rieth et al. | |
| 2013/0052116 A1 | 2/2013 | Barney et al. | |

FOREIGN PATENT DOCUMENTS

| | | | |
|---|---|---|---|
| EP | 2363109 A2 * | 9/2011 | |
| WO | 2007146015 A2 | 12/2007 | |

OTHER PUBLICATIONS

Applicant's draft amendment for discussion purposes only and preliminary argument, Oct. 5, 2015.*
http://www.merriam-webster.com/dictionary/clay, accessed Oct. 7, 2015.*
http://www.turnedoutright.com/2008/01/22/polymer-clay-segment-inlay/, accessed Oct. 7, 2015.*
Charles Ross & Son Company, "Ultra-high shear mixing and deagglomeration," Technology Brief, Mixing Technology Insight #175, Jun. 13, 2012.
Manu Enterprises, "Processing Machines—Chemical Processing Machines and Paint Processing Machines Manufacturer & Exporter" http://www.grinding.in/milling-machines.html, published Jul. 25, 2010.
Quadro Engineering, "Liquids Processing Devision" http://www.quadroytron.com/products_HV.asp, published Dec. 3, 2013.
Charles Ross & Son Company, "Move your media mill process to an ultra-high shear mixer," Technology Brief, Mixing Technology Insight #64, Jul. 18, 2011.
Elementis Specialties, "Rheological Additives in Cosmetics," Dec. 3, 2013.
The State of the Art Report published by the Spanish Patent and Trademark Office on Apr. 14, 2015.

* cited by examiner

*Primary Examiner* — Paul Dickinson
(74) *Attorney, Agent, or Firm* — Michael B. Fein; Eckert Seamans Cherin & Mellott, LLC

(57) ABSTRACT

A method of making a nail polish comprising using a rotor-stator to prepare a suspension base by mixing dry clay and film forming material in a solvent or solvent mixture to make a clay gel, allowing the resultant clay gel to thicken, and letting the thickened clay gel down in additional solvent, film forming polymer, and plasticizer and then adding pigment paste. The rotor-stator can be used before and/or after adding the pigment paste or can be used to make the pigment paste itself. Nail polish cosmetic compositions, UV curable cosmetic nail gel compositions, and nails coated with the compositions.

16 Claims, 2 Drawing Sheets

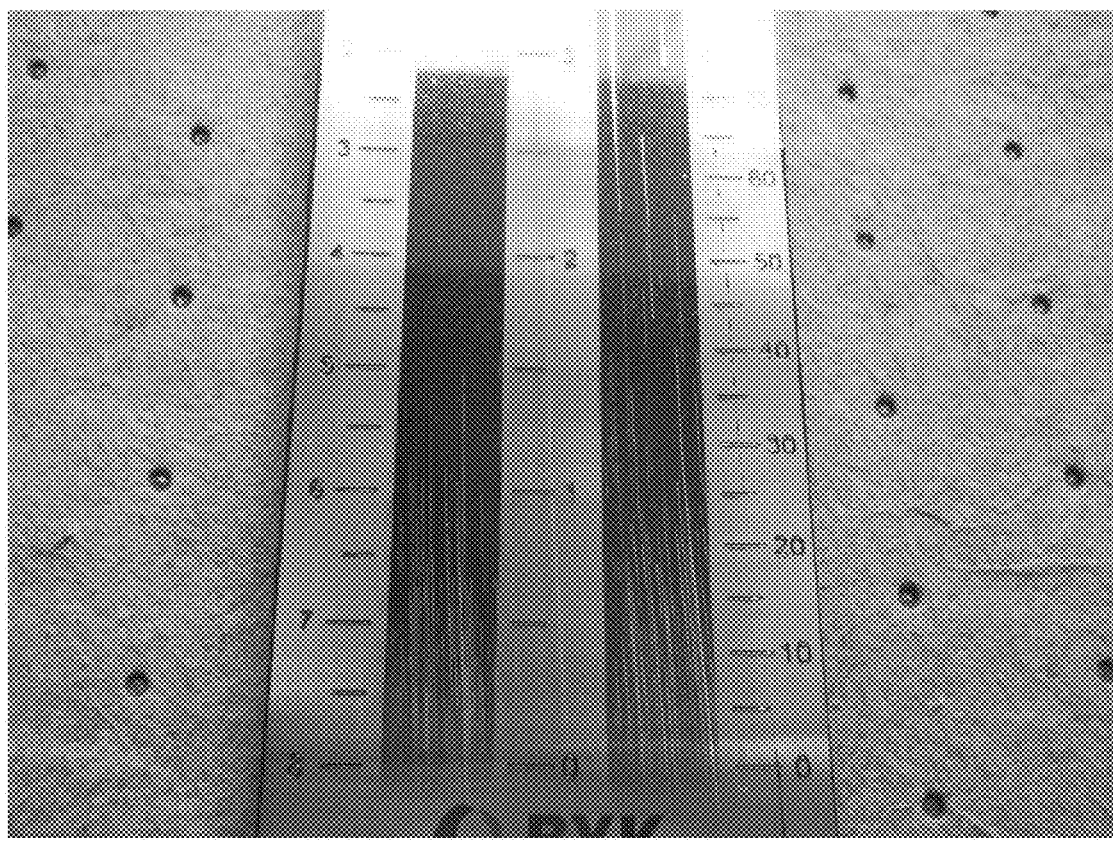
Fig. 1 - Hegman after 2 hours of mixing

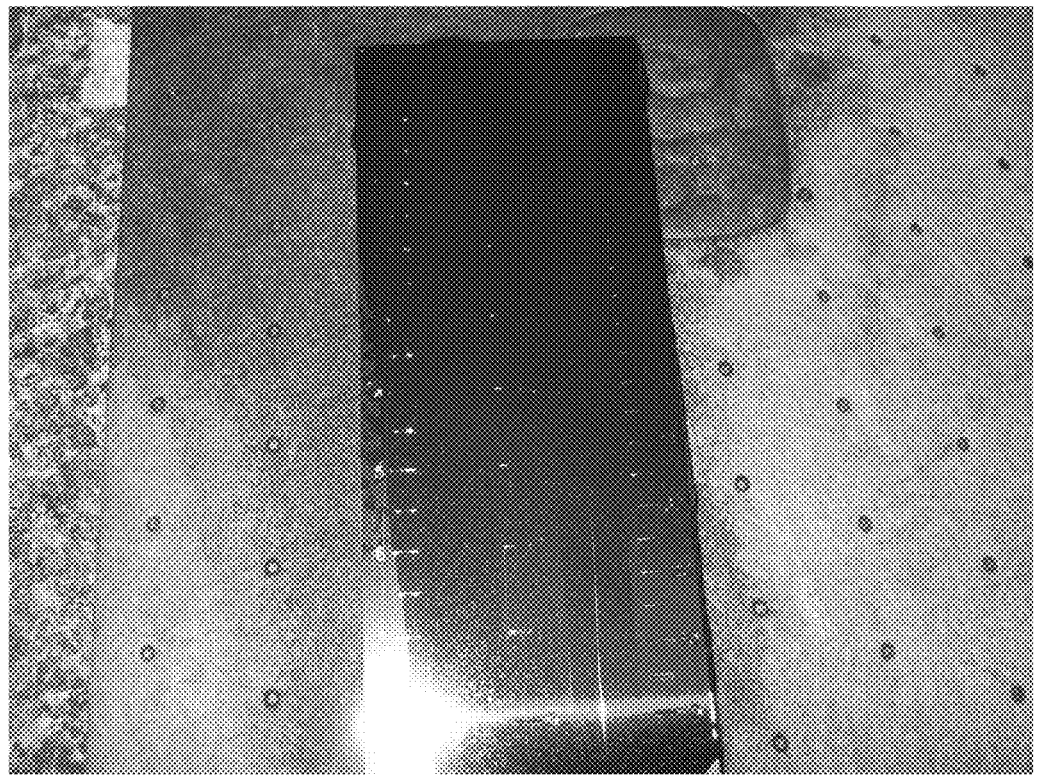
Fig. 2 - Hegman after rotor-stator
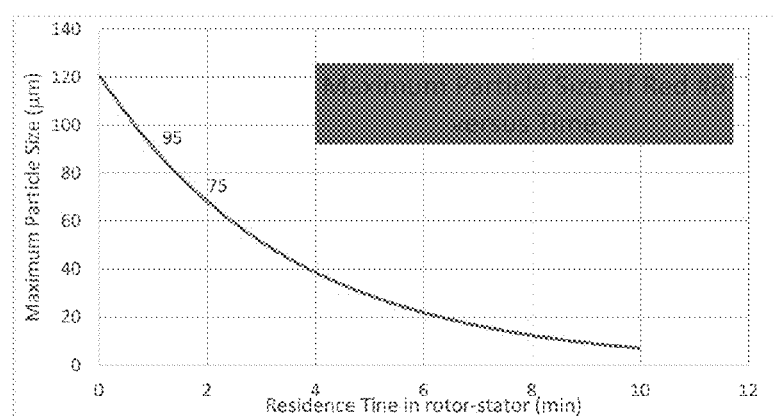
Fig. 3

NAIL POLISH COMPOSITION AND METHOD OF MAKING A NAIL POLISH

CROSS REFERENCE TO RELATED APPLICATIONS

Benefit of U.S. provisional patent application No. 61/824,665 filed May 17, 2013 is claimed.

BACKGROUND OF THE INVENTION

This invention relates to the field of nail polish compositions comprising film forming material, organic solvent, and clay thixotropic agent and methods of making such compositions.

Nail polish for coating human finger and toe nails typically comprises a film forming material such as nitrocellulose, organic solvent such as ethyl acetate, butyl acetate, toluene, and xylene, pigment for color, and clay as a thixotropic agent to provide thickening and prevent settling of pigment. Among the clays which have been used in the art are smectite, organophilic smectite, hectorite, bentonite, mica, montmorillonite, beidellites, saponites, vermiculites, stevensites, laponites, attapulgites, and others. The clays are usually modified with a quaternary amine, imidazoline, amine soap, fatty sulfate, sulfonates, and/or other organic compounds. For example, organically modified hectorite clay is known to be useful for suspending pigment in such nail polish compositions.

During the manufacture of such nail polish a gel of clay, solvent, and film forming material is formed and is then let down into a solvent and film forming material solution. The gel is conventionally subjected to homogination, also known as milling, to reduce the particle size of the clay by breaking up the clay. Typical homoginizers are sold under the brand names Dyno-mill and Gaulins. During the homogination step viscosity is built up over a residence time prior to the let down step.

The homogination/milling step is usually followed by several days or weeks of aging to reach acceptable viscosity prior to the let down step. These periods of time are problematic in high volume manufacturing processes and it has been an object in this art to improve nail polish manufacturing processes by reducing the residence time and aging time for this step.

Pigmented and unpigmented nail polishes are well known. In the case of pigmented nail polishes, pigment is usually added as a paste after the let down step.

SUMMARY OF THE INVENTION

This object and others which will become apparent from the following detailed description are achieved by the present invention which comprises in one aspect a method of making a nail polish comprising using a rotor-stator to prepare a suspension base by mixing dry clay and film forming material in a solvent or solvent mixture to make a clay gel, allowing the resultant clay gel to thicken, and letting the thickened clay gel down in additional solvent, film forming polymer, and plasticizer and then adding pigment paste. The rotor-stator can be used before and/or after adding the pigment paste or can be used to make the pigment paste itself.

In some embodiments the method comprises (A) preparing a suspension base by mixing dry clay and film forming material in a solvent or solvent mixture with a rotor-stator device to deagglomerate the clay to make a clay gel, allowing the resultant clay gel to thicken, and letting the thickened clay gel down in additional solvent, film forming polymer, and plasticizer. In some embodiments the method comprises (B) preparing a colored suspension base by mixing dry clay and film forming material in a solvent or solvent mixture with a mixing device to deagglomerate the clay to make a clay gel, allowing the resultant clay gel to thicken, and letting the thickened clay gel down in additional solvent, film forming polymer, and plasticizer to make a uncolored suspension base and then mixing pigment paste and the uncolored suspension base with a rotor-stator. In some embodiments the invention comprises (C) shearing a suspension base prepared according to (A) or a colored suspension base prepared according to (B) with a rotor-stator. In some embodiments the invention comprises (D) preparing a pigment paste by mixing pigment chips or pigment powder with clay, solvent or solvent mixture, film forming polymer, and plasticizer with a rotor-stator.

In some embodiments the mixing step is conducted in less than 30 seconds. In some embodiments the mixed suspension is allowed to thicken for less than one day prior to letting the resultant thickened suspension down. In some embodiments the mixed suspension is let down immediately after the mixing step which is highly advantageous compared to prior art methods which require days or weeks of standing to allow thickening.

With the use of a rotor-stator device rather than a conventional homogenizer, the required viscosity is unexpectedly achieved more quickly, with less residence time in the mill, and with shorter recovery time.

In another aspect the invention comprises a nail polish comprising the resultant let down suspension of deagglomerated clay.

The method of the invention results in an initial sitting viscosity that is high which helps eliminate pigment settling. The resultant nail polish is improved versus prior compositions in that upon added shear when brushing on the nail viscosity thins to a much more flowable/spreadable coating material, and then when brushing stops viscosity recovers, also referred to as the return viscosity, so the colored nail polish does not drip or run, producing a more flawless coating material.

We have discovered that rather than suspension base or colored suspension base viscosity going down with increased shear as would have been expected, using the rotor-stator, viscosity goes up with increased shear. Selection of viscosity is crucial in making clay gel.

BRIEF DESCRIPTION OF THE DRAWINGS

FIG. 1 is a photo of a pigment paste prepared according to a conventional method and applied to a Hegman gauge, showing streaks.

FIG. 2 is a photo of a pigment paste prepared according to the invention and applied to a Hegman gauge, showing no streaks.

FIG. 3 a graph of the maximum particle size versus the residence time in the rotor-stator.

DETAILED DESCRIPTION

The use of a rotor-stator in the preparation of a nail polish composition is quite unique. The rotor-stator can be used at one or more point in the process of preparing the nail polish compositions, which are improved compared to nail polish compositions prepared with prior art mixing and shearing devices. A rotor-stator is a machine which comprises a rotor which turns at high speed within a stationary stator. As the blades of the rotor pass each port in the stator, they expel material at high velocity into the surrounding mix. They also physically shear particles and droplets, quickly grinding solids and hydraulically shearing droplets. Suitable rotor-stators provide mechanical and hydraulic shear capable of reducing particles/droplets to below 10 microns in size and are preferably multistage rotor-stator units capable of reducing the particle/droplet size to below 5 microns. Units which are most preferable are capable of reducing the particle/droplet size to below 1 micron.

The rotor-stator may be used in preparing a suspension base by mixing dry clay and film forming material in a solvent or solvent mixture with a rotor-stator mixing device to deagglomerate the clay to make a clay gel, allowing the resultant clay gel to thicken, and letting the thickened clay gel down in additional solvent, film forming polymer, and plasticizer.

The rotor-stator may be used in preparing a colored suspension base by mixing dry clay and film forming material in a solvent or solvent mixture with a mixing device to deagglomerate the clay to make a clay gel, allowing the resultant clay gel to thicken, and letting the thickened clay gel down in additional solvent, film forming polymer, and plasticizer to make a uncolored suspension base and then mixing pigment paste and the uncolored suspension base with a rotor-stator.

Suitable rotor-stators are homoginizers having high shear capability, among which are those available from Silverson, Ross, and IKA as well as other manufacturers.

A prepared pigmented or unpigmented suspension base can be improved by further treatment with a rotor-stator.

A pigment paste to be later combined with a suspension base can be prepared by mixing pigment chips or pigment powder by means of a rotor-stator with clay, solvent or solvent mixture, film forming polymer, and plasticizer.

The compositions of the invention comprise solvent, clay suspended in the solvent, and film forming material dissolved in the solvent.

Suitable clays are smectite, organophilic smectite, hectorite, bentonite, mica, montmorillonite, beidellites, saponites, vermiculites, stevensites, laponites and attapulgites. A preferred clay is organically treated hectorite and Bentonite. Preferred brands of organically treated hectorite and Bentonite clays are, for example, Bentone 27V and Tixogel grades M, MPZ, VZV, Tixogel LGM, and MP250.

The film-forming material is generally one or more solvent-borne polymers, for example cellulosic polymers and/or polyurethane polymers. The film-forming polymers can be nonionic, ionic (anionic or cationic), and/or amphoteric (including zwitterionic) polymers. The film-forming polymers are self-curing polymers which do not require chemical reaction or introduction of energy such as ultraviolet light to form an adherent continuum on fingernails or toenails. The film-forming polymer is prepared under substantially anhydrous conditions and is preferably added to the composition which it comprises as a substantially anhydrous solution or other mixture, whether heterogeneous or homogeneous, preferably homogeneous.

Suitable cellulosic film-forming polymers include but are not limited to cellulose esters. Preferred cellulosic polymers are nitrocellulose, cellulose esters such as cellulose acetate, cellulose acetate butyrate, cellulose acetate propionate, and mixtures thereof. More preferred are nitrocellulose, cellulose acetate butyrate, cellulose acetate propionate, and mixtures thereof. Nitrocellulose polymers are most preferred. Exemples of nitrocellulose polymers are nitrocellulose RS types (nitrogen content of 1 1.5-12.2%) from TNC for example -RS ½ second, -RS ¼ second, -RS ⅛ second, -RS ¹⁄₁₆ second.

The nail coating compositions preferably comprise a total of from about 5% to about 20%, more preferably from about 6% to about 20%, even more preferably from about 10% to about 17%, most preferably from about 13% to about 16%, cellulosic polymer.

Suitable film-forming polyurethanes are aromatic polyether polyurethanes, aliphatic polyether polyurethanes, aromatic polyester polyurethanes, aliphatic polyester polyurethanes, aromatic polycaprolactam polyurethanes, aliphatic polycaprolactam polyurethanes, urethane acryl copolymers, siloxane-urethane copolymers, and mixtures thereof. More preferred are aromatic polyether polyurethanes, aliphatic polyether polyurethanes, aromatic polyester polyurethanes, aliphatic polyester polyurethanes, aromatic polycaprolactam polyurethanes, aliphatic polycaprolactam polyurethanes, and mixtures thereof. Aromatic polyether polyurethanes, aliphatic polyether polyurethanes, aromatic polyester polyurethanes, aliphatic polyester polyurethanes and mixtures thereof are even more preferred. Aliphatic polyether polyurethanes, aliphatic polyester polyurethanes, and mixtures thereof are most preferred.

Preferred solvent-borne polyurethanes include Sanres EX519®, Sanres EX499® (hexylene glycol/neopentyl glycol/IPDI [isophorone diisocyanate] copolymer), Sanres 1271 1®, Sanres 6010®, and Sanres 6012® (all of which are available from B.F. Goodrich). The most preferred polyurethane is Sanres EX519®.

The compositions can include additional ingredients conventionally used in the nail polish or UV curable nail gel arts, for example ethylenically unsaturated monomers, oligomers, polymers, and the like. The unsaturated monomers, oligomers, and polymers can be acrylic or methacrylic, for example. The oligomers can be aliphatic polyester or polyether acrylated or methacrylated urethanes or reactive celluloses, for example.

Preferred polyurethanes are those having a number average molecular weight of from about 10,000 to about 80,000, more preferably from about 15,000 to about 50,000, most preferably from about 20,000 to about 35,000.

The present compositions preferably comprise a total of at least about 1.25% film forming polyurethane, e.g., at least about 2%, 3%, 3.5% or 5% film-forming polyurethane. The present compositions preferably comprise a total of from about 1.25% to about 8%, more preferably from about 1.5% to about 5%, most preferably from about 2% to about 4%, film-forming polyurethane.

The nail coating composition is solvent-borne and comprises one or more organic solvents. The composition is substantially anhydrous, preferably comprising less than 2% water, more preferably less than 1% water.

Suitable diluent systems are those which solubilize (i.e., dissolve) the polymers and dry in a reasonable time on nails. The liquid diluent comprises one or more volatile, organic solvents.

Preferred volatile organic solvents have a boiling point at 1 atm of from about 50° C. to about 150° C., more preferably from about 56° C. to about 135° C. Preferred organic solvents are selected from alcohols, esters, ketones, aromatic hydrocarbons, aliphatic hydrocarbons, ethers, and mixtures thereof (more preferably C,-C10, most preferably C2-C4). Alcohols and esters are more preferred, esters being most preferred. Preferred alcohols are monohydric. Preferred monohydric alcohols are ethanol, 1-propanol, and 2-propanol. Preferred ester solvents are butyl, ethyl, isopropyl and propyl acetate, and mixtures thereof. More preferred esters are ethyl, butyl and isopropyl acetate, and mixtures thereof. Other non-limiting examples of suitable organic solvents are benzyl alcohol, amyl acetate, acetone, heptane, wo-butyl acetate, toluene, methyl acetate, 1-butanol, 1-amyl alcohol, 2-butyl alcohol, hexane, and methyl ethyl ketone.

The present compositions preferably comprise from about 55% to about 90%, more preferably from about 62% to about 78%, most preferably from about 66% to about 74%, volatile organic solvent.

Other components useful in the nail polish compositions of the invention are clay activators such as water, diacetone alcohol, isopropyl alcohol, ethanol, citric acid, phosphoric acid, propylene carbonate, toluene, and xylene. Pigment is incorporated in all colored nail polishes but not in clear nail polishes. Pigment is incorporated as a paste added to the let down.

The compositions hereof can further comprise one or more plasticizers such as are known in the art. The plasticizer is generally used in an amount to plasticize the film forming polymers so that the nail polish has acceptable flexibility on the nail. The nail coating compositions preferably comprise from about 3% to about 20%, more preferably from about 5% to about 20%, even more preferably from about 6% to about 15%, most preferably from about 6% to about 10%, plasticizer.

Preferred plasticizer systems are those which reduce brittleness and increase toughness of the nail polish films and which do not inordinately increase viscosity no of the nail polish at the level used.

Preferred plasticizers are selected from the group consisting of polar plasticizers comprising epoxy linkages, linkages comprising a nitrogen atom such as amide, imide, urea and/or urethane linkages (including polar resin plasticizers comprising the foregoing linkages), polyesters, polyester acids (e.g., di- and tri-acids), phthalates, camphor and mixtures thereof. The compositions hereof preferably comprise a plasticizer selected from the group consisting of polar plasticizers comprising amide linkages, polyesters, polyester acids, and mixtures thereof.

Nonlimiting examples of suitable plasticizers are alkyl toluene-sulfonamides, e.g., ethyl toluene-sulfonamide (e.g., Uniplex PX-45 commercially available from Unitex Chemical Corp. of Greensboro, N.C.); toluene sulfonamide formaldehyde ("TSF"); polyesters, e.g., Uniplex 670P (commercially available from Unitex Chemical Corp. of Greensboro, N.C.); polyester acids, e.g., C3-C20, preferably C4-C12, more preferably C6-C10 polyester acids (including di- and tri-acids), such as polyester sebaceates (e.g., Paraplex G-25®, commercially available from C. P. Hall, Bedford Park, Ill.) and polyester adipates (e.g., Paraplex G-50®, commercially available from C. P. Hall); those disclosed in WO 97/00664, Chen et al, assigned to Eastman Chemical Co; phthalates, e.g., diethyl phthalate, dibutyl phthalate, and dioctyl phthalate; nonionic surfactant polymers, e.g. tartrates, (e.g., diethyl tartrate and dibutyl tartrate), phosphates (e.g., diethyl phosphate and dibutyl phosphate) and glycols (e.g., tetraethylene glycol di-2-ethylhexoate, commercially available from C. P. Hall as Tegmer®); camphor; sucrose acetate isobutyrate; and castor oil.

Plasticizer mixtures comprising at least one alkyl toluene-sulfonamide (e.g., Ci-Cio, preferably C -C4 alkyl toluene-sulfonamides) are preferred. A blend of ethyl toluene-sulfonamide and at least one other plasticizer is most preferred.

Preferred compositions comprise from about 3% to about 8% (more preferably from about 4% to about 7%, most preferably from about 4% to about 6%) alkyl toluene-sulfonamide and a total of from about 0.1% to about 6% (more preferably from about 1% to about 5%, most preferably from about 2% to about 3%) of one or more other plasticizers. Preferred other plasticizers are polyesters, polyester acids, camphor, and mixtures thereof.

Particularly preferred compositions comprise a plasticizer selected from the group consisting of polyesters, polyester acids, and mixtures thereof, more preferably selected from the group consisting of polyester acids. Polyester adipates are preferred polyester acids. Such plasticizers are preferably used in an amount of from 0.1% to about 6%, more preferably from about 1% to about 5%, most preferably from about 2% to about 3%.

EXAMPLES

In the following examples all parts and percentages are by weight unless otherwise noted.

Ex. 1

Using Conventional Dyno-Mill Homoginizer or Gaulin High Pressure Homoginizer to Prepare Clay Suspension (Comparative)

A suspension of 36.5 parts ethyl acetate (EA), 35.5 parts butyl acetate (BA), 15 parts ¼ sec nitrocellulose (NC), 7.0 parts organically modified hectorite clay, Bentone 27V brand, 6.0 parts diacetone alcohol were subjected to homoginzation using a Dyno-Mill brand homoginizer. In one experiment the phosphoric acid level was 0.024%. The experiment was repeated three times at a phosphoric acid level of 0.027% added at the end of the suspension base and viscosity was measured at the times indicated for each experiment. The residence times and age in "days since clay made" are set forth in Table 1. In the tables, Ti is an approximation of the resting viscosity of the material. A higher resting viscosity keeps the pigment and mica/pearl particles, which are added as a paste after the let down step, suspended longer. A second viscosity measured after the spindle is rotated for 1 minute at 60 rpm. This viscosity is always lower due to the increased shear imparted by the faster rotation. This relates to how the nail polish will apply when it is sheared with the brush applying it to the nail. The spindle is then slowed to 6 rpm. A third viscosity is the viscosity measured after 1 minute at 6 rpm. Ti is the ratio of the third viscosity to the second. Ti is a measurement of how much the viscosity recovers to the resting value (springs back) in 1 minute. A fast recovery is important so that the particles do not have time to settle before the viscosity recovers. Table 1 includes the data from a prior art Dyno-Mill Homoginizer and Table 2 includes data from a prior art Gaulin Homoginizer.

TABLE 1

Dyno-Mill Homoginizer (Prior Art)

| Dyno-mill Clay Gel | 75% Bead Load | | Controlling Clear | | Suspension Base | | |
|---|---|---|---|---|---|---|---|
| Ethyl acetate | 4036 | 36.5% | 3640 | 28.00% | Clay Gel | 44 | 20.0% |
| Butyl acetate | 3915.8 | 35.5% | 3562 | 27.40% | Controlling Clear | 176 | 80.0% |
| ¼ Sec nitrocellulose | 1656.41 | 15.0% | 2457 | 18.90% | | | |
| ½ Sec nitrocellulose | | | 26 | 0.20% | | | |
| Organically modified hectorite clay (Bentone 27 V) | 772.82 | 7.0% | | | | | |
| Diacetone alcohol | 662.42 | 6.0% | | | | | |
| polyester resin adhesion promotor (Polynex B-75) | | | 2340 | 18.00% | | | |
| Tributylcitrate (Uniplex 83) | | | 975 | 7.50% | | | |
| Total | 11043.45 | 100.0% | 13000 | 100.0% | | 220 | 100.0% |

| Hectorite Gel Used | Viscosities at 25-26° C. (centipoise) | | | | Residence time Sec | Days since clay made | Phosphoric Acid Level |
|---|---|---|---|---|---|---|---|
| | 6 rpms V1 | 60 rpms. V2 | rtn 6 rpms V3 | Ti | | | |
| | 1620 | 636 | 800 | 1.26 | 33 | 15 | 0.024% |
| | 1900 | 660 | 1300 | 1.97 | 66 | 0.67 | 0.027% |
| | 2800 | 810 | 1700 | 2.10 | 66 | 7 | 0.027% |
| | 3520 | 1040 | 2000 | 1.92 | 66 | 29 | 0.027% |

TABLE 2

Gaulin Homoginizer (Prior Art)

| Gaulin Homoginizer Clay Gel | | | Controlling Clear | | Suspension Base | | |
|---|---|---|---|---|---|---|---|
| Ethyl acetate | 4036 | 36.5% | 3640 | 28.00% | Clay Gel | 44 | 20.0% |
| Butyl acetate | 3915.8 | 35.5% | 3562 | 27.40% | Controlling Clear | 176 | 80.0% |
| ¼ Sec nitrocellulose | 1656.41 | 15.0% | 2457 | 18.90% | | | |
| ½ Sec nitrocellulose | | | 26 | 0.20% | | | |
| Organically modified hectorite clay (Bentone 27 V) | 772.82 | 7.0% | | | | | |
| Diacetone alcohol | 662.42 | 6.0% | | | | | |
| polyester resin adhesion promotor (Polynex B-75) | | | 2340 | 18.00% | | | |
| Tributylcitrate (Uniplex 83) | | | 975 | 7.50% | | | |
| Total | 11043.45 | 100.0% | 13000 | 100.0% | | 220 | 100.0% |

| Hectorite Gel Used | Viscosities at 25-26° C. (centipoise) | | | | Days since clay made | Phosphoric Acid Level |
|---|---|---|---|---|---|---|
| | 6 rpms V1 | 60 rpms. V2 | rtn 6 rpms V3 | Ti | | |
| | 580 | 464 | 420 | 0.91 | 3 | 0.025% |
| | 780 | 574 | 500 | 0.87 | 10 | 0.025% |
| | 980 | 524 | 500 | 0.95 | 26 | 0.025% |

Ex. 2

Using Rotor-Stator to Prepare Suspension Base (Invention)

The experiment set forth in Table 1 was repeated except that the phosphoric acid level was 0.026% and the results of the same viscosity measurements are set forth in Table 3. An extreme reduction in time to achieve higher viscosity was observed. The clay gel was thick enough for let down within 10 hours rather than within days or weeks.

TABLE 3

Rotor-stator 3 stages

| Clay Gel | | | Controlling Clear | | Suspension Base | | |
|---|---|---|---|---|---|---|---|
| Ethyl acetate | 5478 | 36.5% | 3640 | 28.00% | Clay Gel | 44 | 20.0% |
| Butyl acetate | 5325 | 35.5% | 3562 | 27.40% | Controlling Clear | 176 | 80.0% |
| ¼ Sec nitrocellulose | 2250 | 15.0% | 2457 | 18.90% | | | |
| ½ Sec nitrocellulose | | | 26 | 0.20% | | | |
| Organically modified hectorite clay (Bentone 27 V) | 1050 | 7.0% | | | | | |
| Diacetone Alcohol | 900 | 6.0% | | | | | |
| polyester resin adhesion promotor (Polynex B-75) | | | 2340 | 18.00% | | | |
| Tributylcitrate (Uniplex 83) | | | 975 | 7.50% | | | |
| total | 15003 | 100.0% | 13000 | 100.0% | | 220 | 100.0% |

| Hectorite Gel Used | Viscosities at 25-26° C. (centipoise) | | | | Residence time Sec | Days since clay made | Phosphoric Acid Level |
|---|---|---|---|---|---|---|---|
| | 6 rpms V1 | 60 rpms. V2 | rtn 6 rpms V3 | Ti | | | |
| | 2760 | 868 | 1820 | 2.10 | 23 | 0 | 0.026% |
| | 4480 | 1122 | 2780 | 2.48 | 23 | 0.67 | 0.026% |
| | 4980 | 1232 | 3180 | 2.58 | 23 | 6 | 0.026% |

As demonstrated by the data in Table 1, which are Comparative and represent prior art, and Table 3, which represents the invention, even though the residence time in the prior art Dyno-Mill experiment is 1½ to 3 times longer than that of the rotor-stator experiment, the suspension base viscosity and Ti are lower for the base containing the Dyno-mill clay gel. Even after 29 days, the Dyno-mill suspension base did not reach the same viscosity that the suspension base developed in 1 day. The V1 and V3 viscosities using the Gaulin homoginizer as shown in Table 2 were significantly lower than comparative V1 and V3 viscosities using the rotor-stator after 3, 10, and 26 days. In fact the roto-stator experiment achieved significantly higher viscosities immediately at 0 days, and at 0.67 days than could be achieved after even 26 days using the Gaulin homoginizer.

Viscosity was lower with the Dyno-Mill experiment for 15 days than the roto-stator experiments for even 0.67 days.

To characterize the materials 3 viscosities are measured because the material is shear thinning. V1 is the viscosity measured after the spindle is rotated for 1 min at 6 rpm. V2 is viscosity measured after 1 minute at 60 RPM. V3 is viscosity measured at 6 rpm "return." Viscosity was measured using a Brookfield LVDVE rotary viscometer. Ti is the ratio of V3 to V2.

Ex. 3

Preparation of Suspension Base

| Suspension Base | % Charge |
|---|---|
| ½ sec Nitrocellulose | 9.7 |
| Hectorite clay | 1.35 |

-continued

| Suspension Base | % Charge |
|---|---|
| Acetyl tributylcitrate | 8.0 |
| ¼ sec Nitrocellulose | 7.5 |
| Polyester resin solution | 11.6 |
| Solution of polyester resin, styrol free | 2.0 |
| Ethyl Acetate | 21.0 |
| Butyl Acetate | 38.5 |
| Benzophenone 1 | 0.20 |
| Citric Acid | 0.025 |
| IPA | 0.225 |

Charge 1935 pounds of ingredients to a 300 gal mix tank fitted with a 12 inch Cowles Blade. Total mix time is 4 hours 40 at the maximum RPM without incorporating air into the batch.

Experiment A uses samples of suspension base before citric acid and IPA added. Some samples have 10% citric acid in IPA post added in lab.

Experiment 3A:

Feed suspension base to rotor-stator set at 60 Hz at a rate of 55 lbs/min.

Viscosity

| Sample # | Acid Used/Process | V1 | V2 | V3 | Ti | rotor-stator (Y/N) |
|---|---|---|---|---|---|---|
| 18A | no acid | 1980 | 986 | 1160 | 1.18 | N |
| 18B | no acid/rotor-stator | 2260 | 906 | 1140 | 1.26 | Y |
| 18C | Citric 100 ppm | 2520 | 980 | 1280 | 1.31 | N |
| 18D | Citric 100 ppm | 2860 | 1074 | 1500 | 1.40 | Y |
| I19C | Citric 100 ppm | 2480 | 888 | 1240 | 1.40 | N |
| 19D | Citric 100 ppm | 2680 | 942 | 1360 | 1.44 | Y |
| 66A | no acid | 2260 | 750 | 980 | 1.31 | N |
| 66B | no acid/rotor-stator | 2440 | 822 | 1120 | 1.36 | Y |
| Average | No rotor-stator | 2310 | 901 | 1165 | 1.296414 | N |
| Average | rotor-stator | 2560 | 936 | 1280 | 1.365298 | Y |
| % Change | | 10.8% | 3.9% | 9.9% | 5.3% | |

Gloss

| | Black | | White | | |
|---|---|---|---|---|---|
| Sample # | Avg 20 | Avg 60 | Avg 20 | Avg 60 | Sample point |
| 18A | 54.53 | 84 | 55.33 | 80.63 | No rotor-stator |
| 18B | 61.9 | 86.27 | 61.73 | 82.5 | rotor-stator |
| 18C | 54 | 83.5 | 54.03 | 80.8 | No rotor-stator |
| 18D | 57.87 | 84.9 | 57.6 | 81.07 | rotor-stator |
| 19C | 52.5 | 82.87 | 53.8 | 79.93 | No rotor-stator |
| 19D | 54.13 | 84 | 53.73 | 80.63 | rotor-stator |
| 66A | 58.1 | 83.93 | 55.87 | 80 | No rotor-stator |
| 66B | 58.9 | 84.67 | 59 | 80.97 | rotor-stator |
| Average | 54.7825 | 83.575 | 54.7575 | 80.34 | No rotor-stator |
| Average | 58.2 | 84.96 | 58.015 | 81.2925 | rotor-stator |
| % Change | 6.2% | 1.7% | 5.9% | 1.2% | |

Experiment 3B:

| Dusty Rose | % | lbs | g |
|---|---|---|---|
| Suspension Base | 88 | 29.04 | 13184.16 |
| Red Oxide Pigment Paste | 1.428 | 0.47 | 213.94 |
| Cosmetic White Pigment Paste | 10.014 | 3.30 | 1500.30 |
| Yellow 5 Pigment Paste | 0.331 | 0.11 | 49.59 |
| FD + C Blue Pigment Paste | 0.228 | 0.08 | 34.16 |
| Total | 100.00 | 33.0 | |

1. Charge about 7 lbs of the suspension base to a 5 gal bucket.
2. Add the pigments and mix thoroughly 3½" pitched blade turbine.
3. Adjust the agitator blade so that it is about 4" from the bottom of the bucket. Adjust the speed to about 250 rpm.
4. Add the rest of the suspension base in and mix until homogeneous.
5. Take an 8 oz. sample of this material
6. Charge the material to the rotor-stator. Set the feed pump to 12 Hz and the rotor-stator to 60 Hz., 12 sec residence time/pass.
7. Purge about 900 grams. Then collect the material.

Viscosity

| Sample | V1 | V2 | V3 | Ti | Temp |
|---|---|---|---|---|---|
| Dusty Rose No rotor-stator | 2480 | 890 | 1160 | 1.3 | 25 |
| rotor-stator 1st Pass- End | 3840 | 1182 | 2000 | 1.69 | 25 |
| % Change | 58.84% | 32.81% | 72.41% | 30.00% | |

| Sample | Black 20 | Black 60 | White 20 | White 60 | Color |
|---|---|---|---|---|---|
| No rotor-stator | 49.4 | 81.2 | 51 | 81.1 | Dusty Rose SB |
| 1st Pass- End | 51.4 | 82.9 | 52.6 | 82.8 | |
| % Change | 4.05% | 2.09% | 3.14% | 2.10% | |

Ex. 4

Preparation of Pigment Paste for Cosmetic Iron Blue Paste with Pigment Chips

| | % |
|---|---|
| Polyester resin solution | 10.00 |
| Acetyl tributylcitrate | 7.50 |
| Bentone 27V clay | 1.49 |
| ¼ sec Nitrocellulose | 2.31 |
| IPA | 0.99 |
| Ethyl Acetate | 22.19 |
| Butyl Acetate | 22.19 |

1. Prepare 7500 grams of slurry is a 5 gal bucket by adding all ingredients except the pigment chips.
2. Slowly add the chips. Mix for 2 hours 3½" pitched blade turbine. The pigment paste then was applied to test strips and appeared streaked as shown in FIG. 1.

3. Charge the material to the rotor-stator. Set the feed pump to 15 Hz and the rotor-stator to 60 Hz. Residence time is set at 13 sec/pass.
4. Purge about 900 grams. Then collect the material.
After treatment in the rotor-stator, and then applying to test strips, the pigment paste appeared unstreaked as shown in FIG. 2.

Ex. 5

Preparation of Red 6 Pigment Paste with Pigment Powder

|  | % |
|---|---|
| Polyester resin solution | 10.00 |
| Acetyl tributylcitrate | 12.50 |
| Hectorite clay | 1.49 |
| Isopropyl Alcohol | 6.78 |
| Ethyl Acetate | 20.71 |
| Butyl Acetate | 20.71 |
| Red 6 Sun Chemical pigment | 12.00 |
| Nitrocellulose | 15.81 |

1. Prepare 7500 grams of slurry is a 5 gal bucket by adding all ingredients except the pigment.
2. Slowly add the pigment. Mix for 30 minutes.
3. Charge the material to the rotor-stator. Set the feed pump to 15 Hz and the rotor-stator to 60 Hz.
4. Purge about 900 grams. Then collect the material.

Gloss

| Sample | Black 20 | Black 60 | White 20 | White 60 | Color | Residence time |
|---|---|---|---|---|---|---|
| 1st Pass | 1 | 10.5 | 1.1 | 11 | Red 6 | 50 sec |
| 2nd Pass-End | 1.9 | 13.9 | 1.9 | 14.2 |  | 50 sec |
| % Change | 90.00% | 32.38% | 72.73% | 29.09% |  |  |

The maximum particle size is estimated based on two data points in FIG. 3.

Ex. 6

Preparation of Clay Composition Using Rotor-Stator

As shown below, when the pre-mixture concentration of clay is increased, from 6.75% to 10% in solvents, and nitrocellulose, higher viscosities are achieved in the suspension base. Therefore the process of deagglomerating the clay particles is greatly improved as the pre-sheared clay level and viscosity is increased, when processed through the rotor-stator. These results are surprising and in contrast to those produced when processed in a conventional high pressure homoginizer. Higher concentration and viscosity of pre-sheared clay solutions reduce their performance and productivity as well as the resulting suspension base viscosity characteristics needed to produce stable pigmented products.

| Run # | 33A (wt %) | 31C (wt %) |
|---|---|---|
| Ethyl Acetate | 32.2 | 21.6 |
| Butyl Acetate | 35.5 | 56.65 |
| Nitrocellulose | 22.3 | 15.0 |
| Hectorite Clay | 10.0 | 6.75 |

Resulting suspension base viscosities when used at 1.35% suspension base in the clay and holding all other ingredients at the same level.

| Clay Gel Used | V1 | V2 | V3 | Ti | Temp | Day of test |
|---|---|---|---|---|---|---|
| 33A 10% clay | 3380 | 1094 | 2040 | 1.86 | 22 | 1 |
| 31C 6.75% clay | 160 | 326 | 100 | 0.31 | 23.1 | 1 |

The present invention, therefore, is well adapted to carry out the objects and attain the ends and advantages mentioned, as well as others inherent therein. While the invention has been depicted and described and is defined by reference to particular embodiments of the invention, such references do not imply a limitation on the invention, and no such limitation is to be inferred. Consequently, the invention is intended to be limited only by the spirit and scope of the appended claims, giving full cognizance to equivalents in all respects.

What is claimed is:

1. A method comprising:
    (A) preparing a suspension base by mixing dry clay and film forming material in a solvent or solvent mixture with a rotor-stator mixing device to deagglomerate the clay to make a clay gel, allowing the resultant clay gel to thicken, and letting the thickened clay gel down in additional solvent, film forming polymer, and plasticizer;
    (B) preparing a colored suspension base by mixing dry clay and film forming material in a solvent or solvent mixture with a mixing device to deagglomerate the clay to make a clay gel, allowing the resultant clay gel to thicken, and letting the thickened clay gel down in additional solvent, film forming polymer, and plasticizer to make a uncolored suspension base and then mixing pigment paste and the uncolored suspension base with a rotor-stator;
    (C) shearing a suspension base prepared according to (A) or a colored suspension base prepared according to (B) with a rotor-stator; or
    (D) preparing a pigment by mixing pigment chips or pigment powder with agglomerated clay, solvent or solvent mixture, film forming polymer, and plasticizer with a rotor-stator to deagglomerate the clay in the mixture of pigment chips or pigment powder, clay, solvent or solvent mixture, film forming plasticizer, and plasticizer.

2. The method of claim 1 comprising mixing the clay gel in (A) or (B) for less than 30 seconds.

3. The method of claim 1 comprising allowing the suspension base of prepared according to (A) or colored suspension base prepared according to (B) to thicken for a period of less than one day.

4. The method of claim 1 comprising letting the suspension base or colored suspension base down immediately after the mixing step.

5. The method of claim 1 wherein the clay is an organoclay.

6. The method of claim 1 wherein the clay is organically treated hectorite.

7. The method of claim 1 wherein the clay is organically treated Bentonite.

8. The method of claim 1 wherein the film-forming material is a solvent borne polymer comprising less than 25 by wt. water.

9. The method of claim 1 wherein the suspension base or colored suspension base comprises 5 to 20% by wt. film forming material.

10. The method of claim 1 wherein the suspension base or colored suspension base comprises 5-20% by wt. film-forming material and the film forming material comprises cellulosic polymer and polyurethane.

11. A composition useful as a cosmetic coating for natural and artificial nails comprising a suspension base, colored suspension base, or pigment paste prepared by
- (A) preparing a suspension base by mixing dry clay and film forming material in a solvent or solvent mixture with a rotor-stator mixing device to deagglomerate the clay to make a clay gel, allowing the resultant clay gel to thicken, and letting the thickened clay gel down in additional solvent, film forming polymer, and plasticizer;
- (B) preparing a colored suspension base by mixing dry clay and film forming material in a solvent or solvent mixture with a mixing device to deagglomerate the clay to make a clay gel, allowing the resultant clay gel to thicken, and letting the thickened clay gel down in additional solvent, film forming polymer, and plasticizer to make a uncolored suspension base and then mixing pigment paste and the uncolored suspension base with a rotor-stator;
- (C) shearing a suspension base prepared according to (A) or a colored suspension base prepared according to (B) with a rotor-stator; or
- (D) preparing a pigment paste by mixing pigment chips or pigment powder with agglomerated clay, solvent or solvent mixture, film forming polymer, and plasticizer with a rotor-stator to deagglomerate the clay in the mixture of pigment chips or pigment powder, clay, solvent or solvent mixture, film forming plasticizer, and plasticizer.

12. The composition of claim 11 comprising pigment.

13. The composition of claim 11 comprising one or more reactive materials selected from the group consisting of monomers, oligomers, and polymers.

14. The composition of claim 11 comprising one or more reactive materials selected from the group consisting of monomers, oligomers, and polymers in the form of a UV curable cosmetic nail coating gel.

15. The composition of claim 11 in the form of a nail polish enamel.

16. A nail coated with the composition of claim 11.

* * * * *